United States Patent
O'Connor

(10) Patent No.: US 8,427,148 B2
(45) Date of Patent: Apr. 23, 2013

(54) SYSTEM FOR COMBINING MAGNETIC RESONANCE IMAGING WITH PARTICLE-BASED RADIATION SYSTEMS FOR IMAGE GUIDED RADIATION THERAPY

(75) Inventor: John P. O'Connor, Andover, MA (US)

(73) Assignee: Analogic Corporation, Peabody, MA (US)

( * ) Notice: Subject to any disclaimer, the term of this patent is extended or adjusted under 35 U.S.C. 154(b) by 463 days.

(21) Appl. No.: 12/651,170

(22) Filed: Dec. 31, 2009

(65) Prior Publication Data

US 2011/0156703 A1    Jun. 30, 2011

(51) Int. Cl.
*G01V 3/00* (2006.01)

(52) U.S. Cl.
USPC .......................................................... 324/307

(58) Field of Classification Search ........... 324/300–322
See application file for complete search history.

(56) References Cited

U.S. PATENT DOCUMENTS

| | | | |
|---|---|---|---|
| 5,672,879 A * | 9/1997 | Glavish .................. | 250/396 ML |
| 6,541,973 B1 | 4/2003 | Danby et al. | |
| 6,677,753 B1 | 1/2004 | Danby et al. | |
| 6,700,468 B2 | 3/2004 | Crozier et al. | |
| 7,196,519 B2 | 3/2007 | Damadian | |
| 7,274,192 B2 | 9/2007 | Havens | |
| 7,586,112 B2 | 9/2009 | Chiba et al. | |
| 7,773,656 B1 * | 8/2010 | Mills ............................... | 372/55 |
| 7,859,264 B2 * | 12/2010 | Wosik et al. .................. | 324/318 |
| 7,889,042 B2 * | 2/2011 | Meinke .......................... | 336/200 |
| 7,960,710 B2 * | 6/2011 | Kruip et al. ................. | 250/492.3 |
| 8,061,016 B2 * | 11/2011 | Maher .............................. | 29/599 |
| 8,106,656 B2 * | 1/2012 | Wosik et al. .................. | 324/318 |
| 2008/0045829 A1 | 2/2008 | Cho et al. | |
| 2009/0234219 A1 | 9/2009 | Kruip | |

OTHER PUBLICATIONS

Day, "Hybrid Imaging System Combines X Rays and Magnetic Resonance to Improve Surgical Procedures," *Physics Today*, Jun. 2005, pp. 22-23.

Raaymakers et al., "Feasibility of MRI guided proton therapy: magnetic field dose effects," *Institute of Physics and Engineering in Medicine*, 2008, pp. 5615-5622.

* cited by examiner

*Primary Examiner* — Dixomara Vargas
(74) *Attorney, Agent, or Firm* — McDermott Will & Emery LLP

(57) ABSTRACT

A hybrid MRI-particle-based therapy system can include as components both a particle radiation therapy system configured to apply a charged particle beam to a region of application in a predetermined direction and also a MRI system including a magnetic field generator for generating a magnetic field in an imaging volume which includes the region of application at the same time that the charged particle beam is applied. The MRI system can be configured with two toroidal magnets or a magnet having apertures to provide access to the region of application for the charged particle beam, and to provide a homogeneous magnetic field in the region of application of the charged particle beam. The particle beam can be positioned to pass through a relatively low-strength portion of the main magnetic $B_0$ field of the MRI system. Related methods of image-guided therapy are also provided by embodiments of the present disclosure.

22 Claims, 5 Drawing Sheets

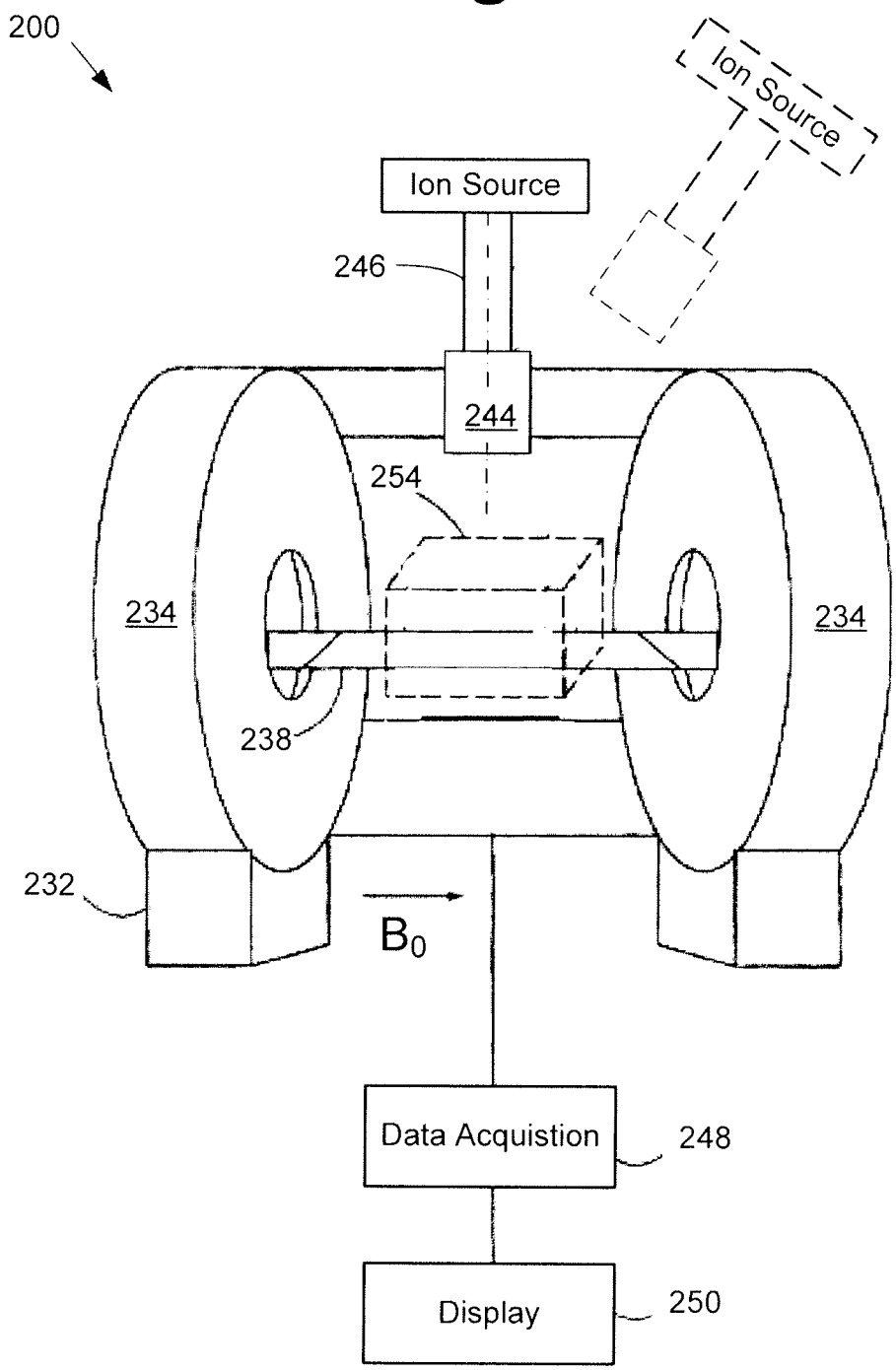

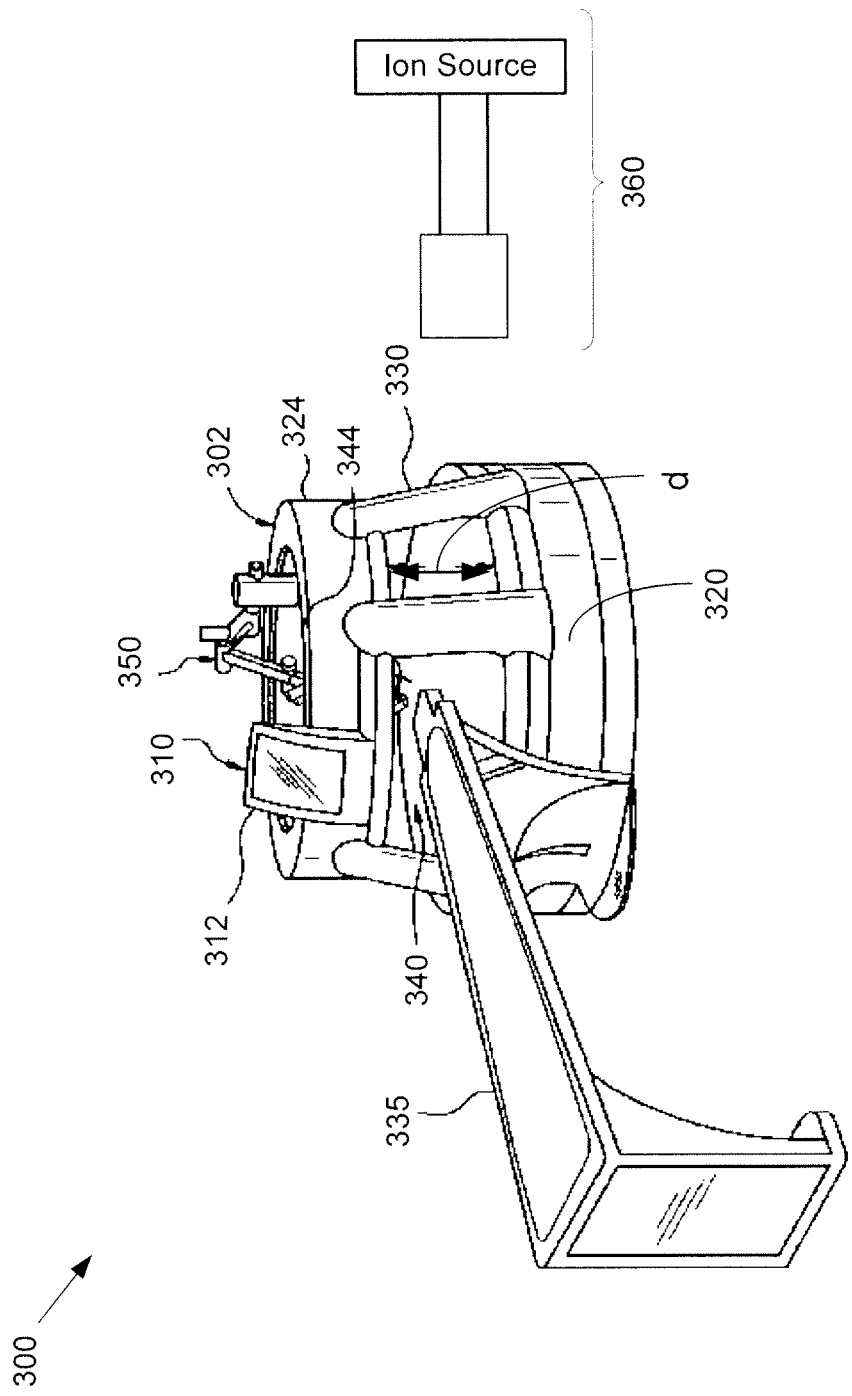

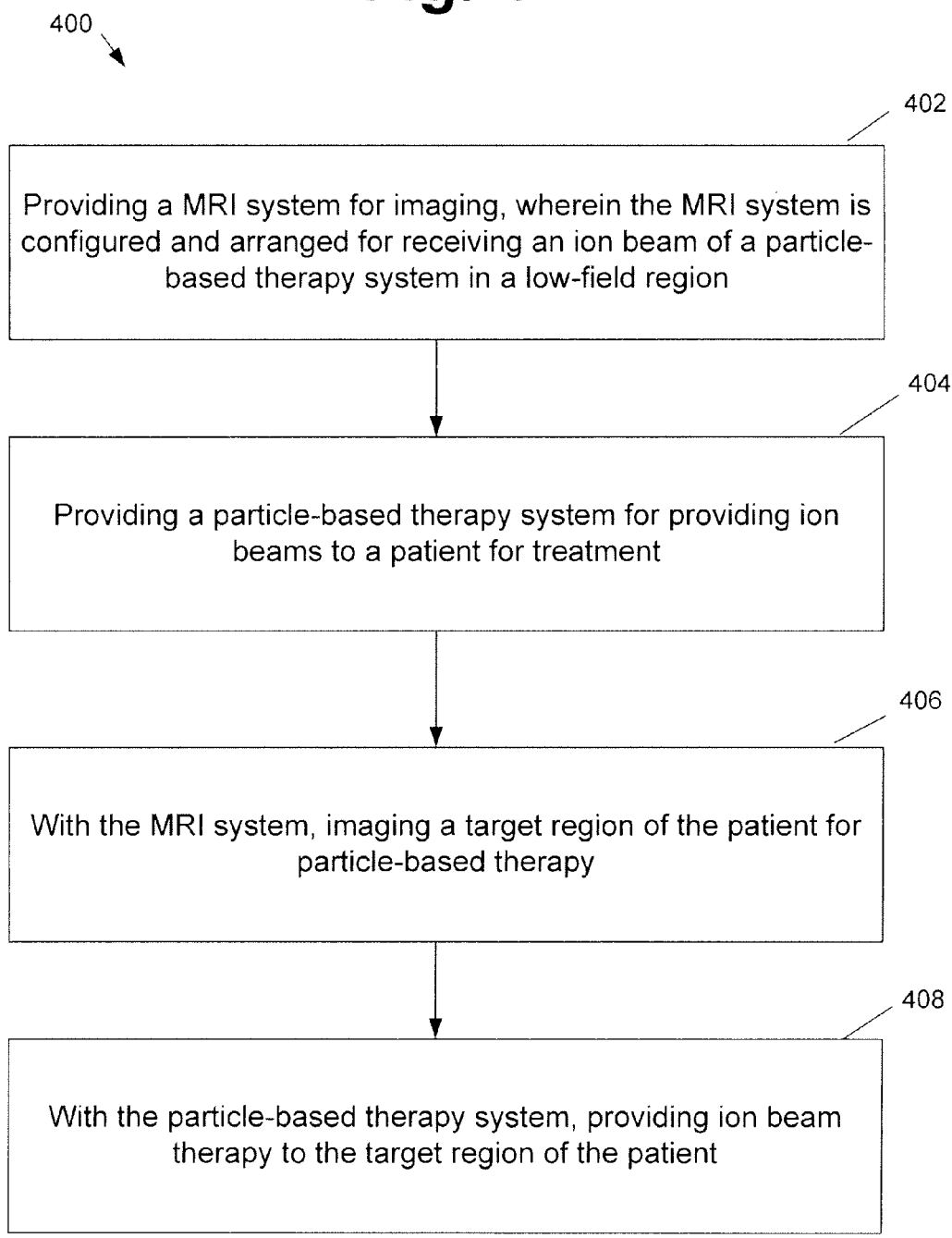

SYSTEM FOR COMBINING MAGNETIC RESONANCE IMAGING WITH PARTICLE-BASED RADIATION SYSTEMS FOR IMAGE GUIDED RADIATION THERAPY

BACKGROUND

For many years, radiation therapy has been an indispensable part of cancer therapy. Especially, X-rays and Gamma rays, consisting of small particles called photons, have been used for attacking the tumor. They remove electrons out of tumor cell atoms and destroy larger molecules within the cells by destroying smaller chemical compounds before. Radiation beams also damage the genetic code, the DNA of the cells and thereby the construction plans for essential proteins. Furthermore, cells cannot replicate any more and consequently, they die. However, the energy is only partly transferred to the tumor. This problem has been partly solved by modern techniques in which photon beams hit the tumor from multiple directions and meet at a defined target where they discharge a maximum of energy. At the same time mobile apertures screen the sensitive healthy tissue from radiation. The so called Intensity Modified Radiation Therapy (IMRT) improves the treatment results of conventional radiotherapy considerably.

Ion radiation does not use photons, but positively charged ions, atomic nuclei which have lost at least one electron from the atomic shell. The particles mainly used are hydrogen atomic nuclei (protons) and carbon atomic nuclei, which are very heavy. This particular type of ions is therefore called heavy ion. Atomic nuclei are accelerated in large devices to about three quarters of the speed of light and shot into the tumor. The depth of penetration can be enhanced by speeding up the ions. Ion beams have always been interesting candidates for radiation therapy, since they have special physical characteristics: When they hit the body they travel very fast through the outer layers and lose hardly any energy before they decelerate in the depth and eventually get stuck and transfer their entire deleterious energy to the surrounding tissue. Scientists call this moment the Bragg peak after its discoverer, the English physicist William Henry Bragg. Therefore, ion beams are well-suited for treating tumors located deeply inside the body. Also, tumors with irregular edges can be scanned accurately to the millimeter with the Intensity-Controlled Raster Scan Method.

Radiation therapy with protons and carbon ion beams has been shown to be an effective treatment for tumors. In addition, such therapy has been shown to result in less damage to surrounding healthy tissue than conventional gamma radiation therapy.

Radiation planning for determining the magnitude and position of a radiation dose to be administered is typically based on previous MRI imaging or CT imaging, which may have taken place at a considerable time period before the therapy takes place. In the intervening period, the tissue to be irradiated may have moved, or changed shape. This may result in the irradiation of healthy tissue and/or missing diseased tissue, which may prevent the disease from moving to a remission.

In the past several years, techniques have been developed for more precisely targeting incident radiation upon tumors in a human body. Such techniques have been achieved by using advances in X-ray sources and collimation systems. Also, imaging of the body has been improved by optimizing the related targeting algorithms by mapping the body with CT systems and inputting the data into the algorithm(s).

Recently, MRI systems and X-ray systems have been presented that combine attributes of both types of imaging.

Unfortunately, for the treatment of tumors such as those from malignant cancers, X-ray therapy does not possess the precision of dose administration or stopping power that particle-based therapy has. It is difficult or impossible to irradiate targeted tissue and transfer the energy of the radiation to the desired tissue in a precise manner, as X-rays by their nature as highly energetic photons, pass through most soft tissue unimpeded.

While radiations systems and methods do exist to irradiate tumors and other tissue with particles, e.g., protons, carbon nuclei, etc., such charged particles by definition will naturally deflect from a straight line trajectory in the presence of a high-strength magnetic field such as produced by common MRI systems. Such deflection can render ion beam targeting inaccurate, and can potentially cause the irradiation of healthy tissue while at the same time diseased tissue can escape radiation exposure.

SUMMARY

Embodiments of the present disclosure address shortcomings described previously by providing MRI systems in tandem with particle-based therapy systems that can provide particle radiation suitable for killing tumors and other tissue. A hybrid MRI-particle-based therapy system, in accordance with exemplary embodiments, can include as components both a particle radiation therapy system configured and arranged to apply a charged particle beam to a region of application in a predetermined direction and also a MRI system including a magnetic field generation system or means for generating a magnetic field in an imaging volume which includes the region of application at the same time that the charged particle beam is applied. The MRI system can be configured and arranged with two donut-shaped magnets or a magnet having apertures to provide access to the region of application for the charged particle beam, and to provide a homogeneous magnetic field in the region of application of the charged particle beam. The particle beam can be positioned to pass through a relatively low-strength portion of the main magnetic $B_0$ field of the MRI system. Related methods of image-guided therapy are also provided by embodiments of the present disclosure.

As a result, such systems can provide real-time targeting information for the accelerator control system with respect to tumor location. Advantages of such systems compared to photon-based systems include that the radiation source, acceleration system, steering magnets and collimation system may be placed outside of the high-field region of the MRI unit.

These, as well as other components, steps, features benefits, and advantages, will now become clear from a review of the following detailed description of illustrative embodiments, the accompanying drawings, and the claims.

BRIEF DESCRIPTION OF DRAWINGS

The drawings disclose illustrative embodiments. They do not set forth all embodiments. Other embodiments may be used in addition or instead. Details that may be apparent or unnecessary may be omitted to save space or for more effective illustration. Conversely, some embodiments may be practiced without all of the details that are disclosed. When the same numeral appears in different drawings, it refers to the same or like components or steps.

Aspects of the disclosure may be more fully understood from the following description when read together with the accompanying drawings, which are to be regarded as illustrative in nature, and not as limiting. The drawings are not necessarily to scale, emphasis instead being placed on the principles of the disclosure. In the drawings:

FIG. 2 depicts a schematic diagram of a component MRI system according to an exemplary embodiment of the present disclosure for use in conjunction with a component particle therapy system;

FIG. 3 depicts an alternate embodiment of a component magnetic MRI system, in accordance with the present disclosure; and FIG. 4 depicts a block diagram of a method of image guided radiation therapy, in accordance with an exemplary embodiment of the present disclosure.

Figure 1A:
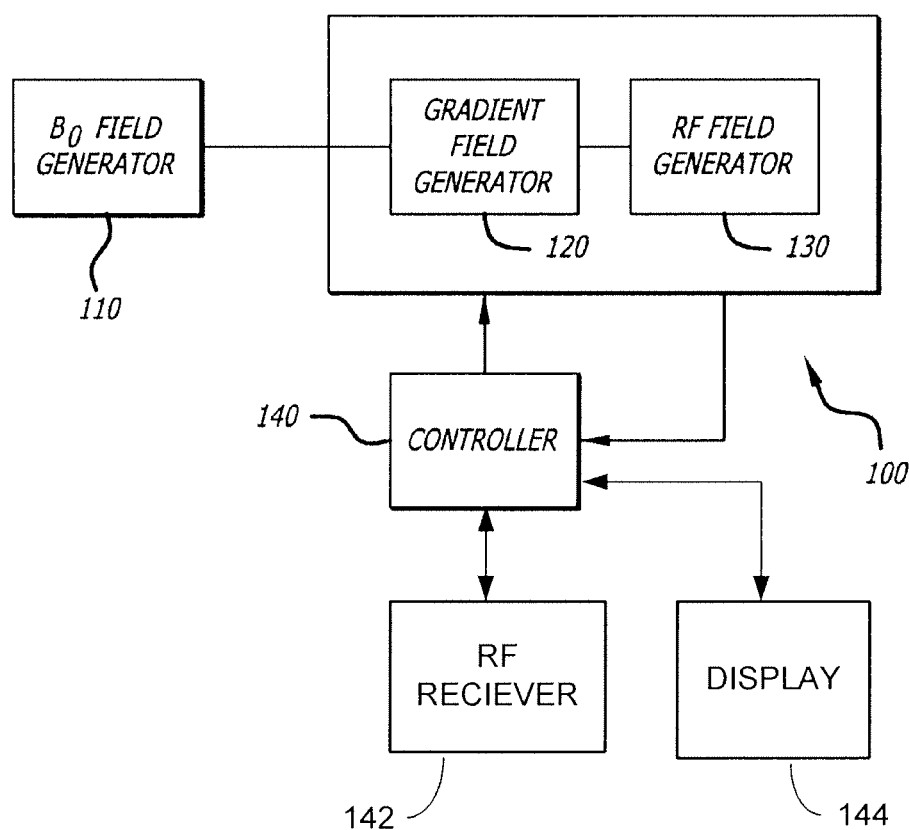
FIG. 1 includes FIGS. 1A and 1B, which together illustrate schematic views of functional blocks of a hybrid MRI-particle therapy system, in accordance with exemplary embodiments of the present disclosure.

While certain embodiments are depicted in the drawings, one skilled in the art will appreciate that the embodiments depicted are illustrative and that variations of those shown, as well as other embodiments described herein, may be envisioned and practiced within the scope of the present disclosure.

DETAILED DESCRIPTION OF ILLUSTRATIVE EMBODIMENTS

Illustrative embodiments are now discussed. Other embodiments may be used in addition or instead. Details that may be apparent or unnecessary may be omitted to save space or for a more effective presentation. Conversely, some embodiments may be practiced without all of the details that are disclosed.

Embodiments of the present disclosure provide for hybrid MRI-particle-based therapy systems for the treatment of cancer and other disease. Such hybrid systems can include as components both a particle radiation therapy system configured and arranged to apply a charged particle beam to a region of application in a predetermined direction and also an MRI system including a magnetic field generation system or means for generating a magnetic field in an imaging volume which includes the region of application at the same time that the charged particle beam is applied. The MRI systems can be configured and arranged with two donut or torroidal magnets or a magnet having apertures to provide access to the region of application for the charged particle beam, and to provide a homogeneous magnetic field in the region of application of the charged particle beam. The particle beam can be positioned to pass through a relatively low-strength portion of the main magnetic $B_0$ field of the MRI system. Related methods of image-guided therapy are also provided by embodiments of the present disclosure.

According to the present disclosure, ion therapy, e.g., using protons or carbon nuclei, can be provided in conjunction with an MRI system. For this, the incident ion beam can be caused to pass through a low-field region of the MRI magnet(s) to ensure that the impact of the magnetic field on the ion beam is minimized. For example, for a 0.35 T MRI system, a proton beam can be caused to pass (or steered) through a region of the magnetic field that is of approximately 35 Gauss (or, $\frac{1}{100}$ of the maximum field strength). This would ensure a worst case impact of less than 2 mm deflection of the ion beam due to the magnetic field effects for targeting purposes. Such a deflection can become more pronounced for heavier ions. As another example, with a heavy-ion based therapy, such as carbon or oxygen nuclei, e.g., a 450 MeV carbon beam, the impact of a 0.35 T field may be approximately 4 mm for a worst case scenario. Because such a deflection may be considered too great, the carbon beam may be passed through a region of the MRI magnetic field that is less than 0.1 T to ensure a lesser beam deflection, e.g., ~1 mm, which may be acceptable for real-time imaging.

With combination of an MRI unit and a particle-based therapy system, in accordance with the present disclosure, true image guided radiation therapy can be realized.

Figure 1B:
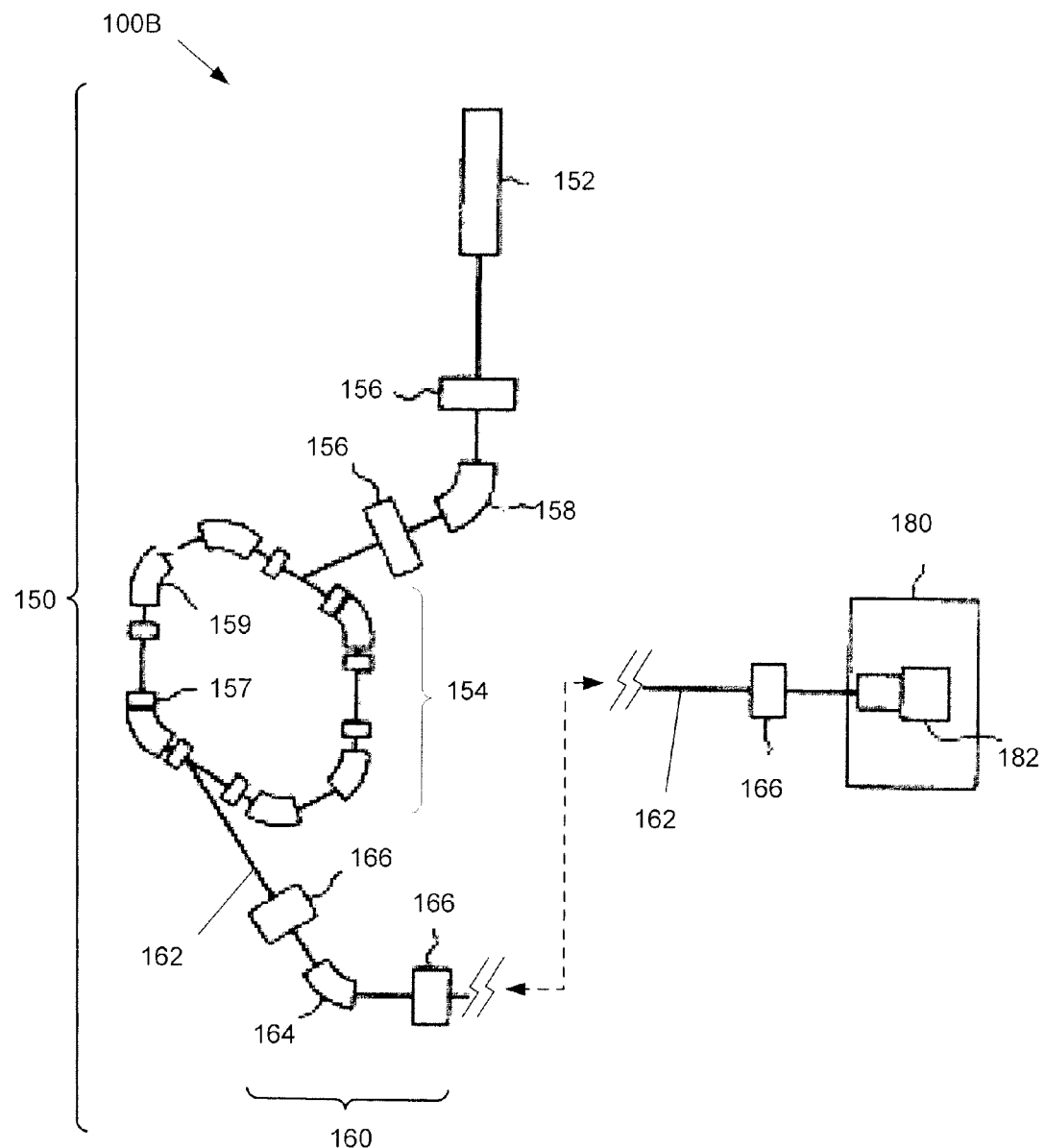

FIGS. 1A and 1B together illustrate functional blocks of a hybrid MRI-particle therapy system, in accordance with exemplary embodiments of the present disclosure. FIG. 1A illustrates a functional block diagram that provides a schematic overview of an MRI apparatus 100A in accordance with an embodiment of the present disclosure. FIG. 1B illustrates a functional block diagram that provides a schematic overview of a particle therapy apparatus 100B in accordance with an embodiment of the present disclosure.

Referring to FIG. 1A, briefly, the MRI system 100A can include a static field generator 110, a gradient field generator 120, an RF excitation field generator 130, and a controller 140 that controls the operation of the gradient field generator 120 and the RF excitation field generator 130. The controller also analyzes or processes the FID (free induction decay) signals received by a receiver (not shown).

The static field generator 110 generates a strong static magnetic field $B_0$, which is used to line up nuclear spins in a target object (whose MRI image is being generated by the apparatus 100) along $B_0$. The gradient field generator 120 generates a gradient field $G(r)$, which is superimposed on the static field $B_0$, so that nuclei in a selected plane can be excited by a proper choice of the frequency spectrum of the transverse RF excitation field. The RF excitation field generator 130 generates an RF excitation field $B_1$. When $B_1$ is applied to the object, typically as an RF excitation pulse transverse to $B_0$, the nuclei become excited (due to the RF energy imparted by the RF excitation pulse), so that the nuclear spins rotate by a flip angle. Subsequently, the excited nuclei gradually return to alignment with the static field $B_0$, giving up the excitation energy in the form of weak but detectable FID signals, which are processed by the controller 140 to produce images of the target object.

The controller 140 controls the operation of the MRI apparatus 100, including but not limited to the generation of the fields $G(r)$, and $B_1$, as well as the processing of the FID signals resulting from the de-excitation (precession and relaxation) of the nuclei in the object. An RF receiver can detect RF energy emitted by the object tissue under consideration after application of the initial RF pulses from the RF Field Generator 130. A display 144 can display the resulting MRI images.

Referring now to FIG. 1B, a functional block diagram is depicted of a particle therapy system 100B in accordance with exemplary embodiments of the present disclosure. Particle therapy system 100B can include a charged particle beam generator 150, a beam transport system 160 connected to the downstream or output side of the charged particle beam generator 150, and a delivery locale 180, including an irradiation apparatus 182. Suitable particle systems are described, for example, in U.S. Pat. No. 7,586,112, which is incorporated herein by reference in its entirety. Intermediate portions of beam transport system 160 are omitted (as indicated by broken lines) for the sake of clarity.

The particle therapy apparatus 100B can include a charged particle beam generator 160 with an ion source (not shown), a pre-stage charged particle beam generator (linear accelerator or "linac") 152, and a synchrotron 154. Ions (e.g., proton or carbon ions) generated from the ion source are accelerated by the pre-stage charged particle beam generator (e.g., a linear charged particle beam generator) 152. An ion beam (e.g., proton beam or carbon beam) emitted from the pre-stage charged particle beam generator 152 enters the synchrotron 154, e.g., through quadrupole magnets 156 and/or a bending magnet 158. The ion beam in the form of a charged particle beam is accelerated in the synchrotron 154 in which energy is given to the ion beam with radio-frequency (RF) power applied from an RF cavity (not shown). After energy of the ion beam circulating in the synchrotron 154 has been increased up to a desired setting level (e.g., 100 to 250 MeV), an RF wave is applied to the circulating ion beam from an RF knockout electrode (not shown) for beam extraction. With the application of the RF wave, the ion beam is caused to exit the synchrotron 154 through a beam extraction deflector (not shown). At the time of extracting the ion beam, currents supplied to magnets, such as quadrupole magnets 157 and bending magnets 159, disposed in the synchrotron 154 are held at setting values, and therefore the related separatrix is also held substantially constant. The extraction of the ion beam from the synchrotron 154 can be stopped by ceasing the application of the RF power to the RF knockout electrode. The ion beam then is supplied through the beam transport system 160 to supplied to the delivery locale 180, with irradiation apparatus 182, for application to a patient.

With continued reference to FIG. 1B, the ion beam extracted from the synchrotron 154 can be transported to the downstream side through the beam transport system 160. The beam transport system 160 has a beam line 162 and can include a bending magnet 164 and quadrupole magnets 166, which are successively arranged on the beam line 162 in this order from the upstream side in the direction of beam advance.

The irradiation apparatus can include a casing or housing (not shown) and a nozzle through which the ion beam exits. The housing can include one or more bending or scanning magnets, a scatterer device, e.g., one or more wire chambers, a ring collimator, a patient collimator, a bolus (compensator), etc., which are arranged therein.

The ion beam introduced to the irradiation apparatus 180 can have an irradiation field that is roughly collimated by the ring collimator in the irradiation apparatus 180 and is shaped by the patient collimator to match the shape (profile) of a diseased part in the planar direction perpendicular to the direction of beam advance (propagation direction). Further, the ion beam can have a penetration depth that is adjusted by the bolus in match with the maximum depth of the diseased part in the body of the patient, e.g., lying on a treatment couch. The ion beam thus formed by the irradiation apparatus 180 can have a dose distribution optimum for particle therapy to the diseased tissue, e.g., tumor, of the patient. The energy of the irradiated ion beam is consequently released to the target tissue.

Carbon ions may be used in exemplary embodiments. Due to less depth and lateral scattering, carbon ions can result in an even sharper Bragg peak than protons. While protons are comparable to photons considering their radiobiological beam properties, carbon ions show a superior treatment in this aspect as well. Due to the higher relative biological effectiveness (RBE) of carbon ions, the number of treatment fractions (irradiations) can be decreased when using carbon ions.

FIG. 2 depicts a schematic diagram of a component MRI system 200 according to an exemplary embodiment of the present disclosure for use in conjunction with a component particle therapy system, e.g., as shown and described for FIG. 1B. As shown in FIG. 2, MRI system 200 can include an open-bore double-donut interventional MRI unit 232 including torroidal magnets 234, an enclosure or frame structure 236 (e.g., in an upper horizontal configuration), a patient support 238, and a bridge 240 below the patient support 238. The magnets 234 provide a static or main magnetic field $B_0$ in the direction of the arrow. Not shown are standard additional elements such as gradient coils, gradient amplifiers, radio frequency (RF) coils, RF transmitters, data acquisition and processing electronics, and a display. Suitable open-bore double-donut MRI magnets and related components include those described in U.S. Pat. No. 6,975,895, which is incorporated herein by reference in its entirety.

With continued reference to FIG. 2, added to MRI unit 232 are an ion source, e.g., of FIG. 1B, connected to an irradiation apparatus 244 by suitable connection 246. Data acquisition and processing electronics 248, and a display 250 are also shown. The MRI field of view (FOV) is shown by the dotted lined box designated by the reference character 254. MR images can be of the MRI FOV 254, e.g., patient tissue within the FOV 254.

The ion irradiation apparatus 244 can be positioned so as to irradiate a patient from a desired direction (a beam axis is indicated). For example, irradiation apparatus can be positioned on an upper horizontal enclosure 252, for some applications, as shown. The irradiation apparatus can of course be positioned along other orientations, e.g., as shown by dashed lines. For exemplary embodiments, irradiation apparatus 244 can be mounted on a movable and adjustable gantry, such as described in U.S. Pat. No. 7,473,913, which is incorporated herein by reference in its entirety.

As can be seen in FIG. 2 (and FIG. 1B), an advantage that is provided is that the radiation source, acceleration system, steering magnets, and collimating system can be placed outside of high field region of the associated MRI unit/system.

In operation of system 200, the preferred placement of the ion beam relative to the MRI magnetic field may require repositioning of the patient between ion beam bursts or use of a multiple beam line assembly to enable targeting from multiple angles. For some applications, when irradiation with the ion beam occurs, the MRI system can be turned off, or only the main magnetic field of the MRI system may be present; other elements, such as the magnetic field gradients and RF magnetic fields, can be inactive.

Embodiments of the present disclosure can provide various additional components for steering the ion beam to counteract the beam deflection induced by the MRI $B_0$ field (or, possibly, the $B_1$ field as well). Steering magnets (not shown) can be included and accordingly be used for such a purpose.

Referring now to FIG. 3, an alternate embodiment of a component magnetic resonance imaging (MRI) system 300 is depicted having a MRI magnet 302 and a control system 310 for the control and operation thereof. A particle-based therapy system 360 including an ion source is also shown. Control system 310 can include a console 312, e.g., for controlling x, y and z-axis gradient magnetic field power supplies (not specifically shown) for powering magnet 302, as well as transmit and receive circuitry (specifically shown) for controlling the RF pulses to RF coils (not specifically shown). Console 312 can also provides overall control for processing and displaying the nuclear magnetic resonance signals during a MR guided interventional procedure. Of course, the position of console 312 as shown in the drawing is for ease of description, and the position of the console 312 can be located as desired and can take into account other system components such as those of particle therapy system, e.g., as shown and described for FIG. 1B.

Magnet 302 can includes a lower (first) section 320 and an upper (second) section 324, separated by a distance "d" via supports 330. A table 335 can enable a patient (not specifically shown) to be moved between supports 330 via one of several side openings 340 into the region between lower 320 and upper 325 sections. The upper section 324 of magnet 302 can be configured with a central opening 344. Openings 340 and 344 can provide access to the patient for equipment, such as interventional apparatus (physician robotic arm for example) 350, and for physicians and other interventional personnel. Suitable open-bore double-donut MRI magnets, systems, and related components can include those described in U.S. Pat. No. 7,274,192, which is incorporated herein by reference in its entirety; which described systems can provide for a MR guided interventional system that is capable of producing a 1.5 Tesla field strength. The ion source 360 can be configured to direct ions through a relatively low-strength portion of the field of the magnet 302, e.g., through the gap indicated by "d".

FIG. 4 depicts a block diagram of a method 400 of image guided radiation therapy, in accordance with an exemplary embodiment of the present disclosure. For method 400, MRI system can be provided for imaging, wherein the MRI system is configured and arranged for receiving an ion beam of a particle-based therapy system in a low-field region of the MRI system, e.g., less than or equal to 0.5 T, as described at 402. A particle-based therapy system can be provided for providing ion beams to a patient, as described at 404. Suitable proton beam sources and related systems are described in U.S. Patent Application Serial No. 2009/0189095, which is incorporated herein by reference in its entirety. Suitable carbon sources and related systems are described, for example, in U.S. Pat. No. 7,586,112, which is incorporated herein by reference in its entirety.

Continuing with the description of method 400, imaging of the target area of the patient can be performed with the MRI system, as described at 406. Ion therapy can be provided to the target region of the patient with the particle-based therapy system, as described at 408. Suitable ions can include protons, carbon nuclei, and oxygen nuclei, to name a few examples. Others may be used within the scope of the present disclosure. The particle-based treatment can take place before or after or concurrently with use of the MRI system.

Accordingly, embodiments of the present disclosure can provide for true image guided radiation therapy by combination of a MRI unit and a particle-based therapy system.

The components, steps, features, benefits and advantages that have been discussed are merely illustrative. None of them, nor the discussions relating to them, are intended to limit the scope of protection in any way. Numerous other embodiments are also contemplated. For example, while embodiments described herein have included reference to separate MRI magnets, other embodiments can include a single MRI magnet with apertures formed therein to accept passage of incident ion beam(s). Moreover, magnet configurations of MRI systems can include antenna or probes configured and arranged for travelling wave MRI, in exemplary embodiments. Such probes can include two orthogonal loop antennas configured and arranged to propagate and receive travelling radio-frequency (RF) waves. Additionally, embodiments of the present disclosure can have fewer, additional, and/or different components, steps, features, benefits and advantages than as expressly described herein. These also include embodiments in which the components and/or steps are arranged and/or ordered differently.

In reading the present disclosure, one skilled in the art will appreciate that embodiments of the present disclosure, such as targeting, imaging, and/or control algorithms, can be implemented in hardware, software, firmware, or any combinations of such, and over one or more networks. Moreover, embodiments of the present disclosure can be included in or carried by various signals, e.g., as transmitted over a wireless RF or IR communications link or downloaded from the Internet.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

All articles, patents, patent applications, and other publications which have been cited in this disclosure are hereby incorporated herein by reference.

The phrase "means for" when used in a claim is intended to and should be interpreted to embrace the corresponding structures and materials that have been described and their equivalents. Similarly, the phrase "step for" when used in a claim embraces the corresponding acts that have been described and their equivalents. The absence of these phrases means that the claim is not intended to and should not be interpreted to be limited to any of the corresponding structures, materials, or acts or to their equivalents.

Nothing that has been stated or illustrated is intended or should be interpreted to cause a dedication of any component, step, feature, object, benefit, advantage, or equivalent to the public, regardless of whether it is recited in the claims.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents.

What is claimed is:

1. A system for image guided radiation therapy comprising:
    a particle-based therapy system configured and arranged to supply an ion beam to a target region of a patient;
    a magnetic resonance imaging (MRI) system having a MRI field of view (FOV) and comprising a magnet for generating a static magnetic field, wherein the MRI system is configured and arranged for receiving an ion beam from the particle-based therapy system in a low-field region;
    one or more steering magnets configured and arranged to steer the ion beam; and
    a controller configured and arranged to steer the ion beam for compensation of a field deflection produced by the main field of the MRI system.

2. The system of claim 1, wherein the low-field region of the MRI system is about 0.5 T in strength.

3. The system of claim 1, wherein the magnet of the MRI system comprises two torroidal magnets spaced apart and concentrically configured about an axis.

4. The system of claim 3, wherein the axis is substantially aligned with a longitudinal axis of a patient support that is configured and arranged to support the patient during treatment.

5. The system of claim 4, wherein an irradiation apparatus of the particle-based therapy system is configured and arranged to irradiate a target region of the patient along a propagation axis substantially perpendicular to the longitudinal axis of the patient support.

6. The system of claim 1, wherein the magnet of the MRI system comprises a cylindrical magnet with one or more apertures configured and arranged to permit the ion beam to impinge on the patient.

7. The system of claim 6, wherein the two or more apertures comprise two opposing apertures.

8. The system of claim 7, wherein the two apertures are rectangular.

9. The system of claim 7, wherein the two apertures are elliptical.

10. The system of claim 1, further comprising a movable gantry for adjustably positioning an irradiation apparatus of the particle-based therapy system.

11. The system of claim 1, wherein the particle-based therapy system is configured and arranged to provide a proton beam.

12. The system of claim 1, wherein the particle-based therapy system is configured and arranged to provide a beam of carbon ions.

13. The system of claim 1, wherein the particle-based therapy system is configured and arranged to provide a beam of oxygen ions.

14. A method of image guided radiation therapy comprising:
providing a particle-based therapy system for providing an ion beam to a target region of a patient;
providing a MRI system for imaging, wherein the MRI system is configured and arranged for receiving an ion beam of the particle-based therapy system in a low-field region;
with the MRI system, imaging a target region of the patient for particle-based therapy;
with the particle-based system, providing an ion beam to the target region of the patient;
providing one or more steering magnets configured and arranged to steer the ion beam; and
with a controller, steering the ion beam for compensation of a field deflection produced by the main field of the MRI system.

15. The method of claim 14, wherein the low-field region of the MRI system is about 0.5 T in strength.

16. The method of claim 14, wherein the magnet of the MRI system comprises two torroidal magnets spaced apart and concentrically configured about an axis.

17. The method of claim 16, wherein the axis is substantially aligned with a longitudinal axis of a patient support that is configured and arranged to support the patient during treatment.

18. The method of claim 17, wherein an irradiation apparatus of the particle-based therapy system is configured and arranged to irradiate a target region of the patient along a propagation axis substantially perpendicular to the longitudinal axis of the patient support.

19. The method of claim 14, wherein the magnet of the MRI system comprises a cylindrical magnet, and further comprising providing the cylindrical magnet with one or more apertures configured and arranged to permit the ion beam to impinge on the patient.

20. The method of claim 14, wherein the particle-based therapy system is configured and arranged to provide a proton beam.

21. The method of claim 14, wherein the particle-based therapy system is configured and arranged to provide a beam of carbon ions.

22. The method of claim 14, wherein the particle-based therapy system is configured and arranged to provide a beam of oxygen ions.

* * * * *